United States Patent [19]

Hussein

[11] Patent Number: 4,470,407

[45] Date of Patent: Sep. 11, 1984

[54] ENDOSCOPIC DEVICE

[75] Inventor: Hany M. G. Hussein, Lindenhurst, Ill.

[73] Assignee: Laserscope, Inc., Santa Ana, Calif.

[21] Appl. No.: 357,150

[22] Filed: Mar. 11, 1982

[51] Int. Cl.³ .......................... A61B 1/06; A61B 17/36
[52] U.S. Cl. ..................................... 128/6; 128/303.1; 128/398
[58] Field of Search ........................ 128/6–8, 128/734, 303.1, 395–398, 4, 5; 604/103

[56] References Cited

U.S. PATENT DOCUMENTS

| 3,162,190 | 12/1964 | Gizzo | 128/6 |
| 3,448,739 | 6/1969 | Stark et al. | 604/103 X |
| 4,072,147 | 2/1978 | Hett | 128/395 X |
| 4,146,019 | 3/1979 | Bass et al. | 128/6 |
| 4,224,929 | 9/1980 | Furiheta | 128/5 |
| 4,313,431 | 2/1982 | Frank | 128/7 |

FOREIGN PATENT DOCUMENTS 2848484 5/1979 Fed. Rep. of Germany .......... 128/6

Primary Examiner—Lee S. Cohen

[57] ABSTRACT

An endoscopic device is disclosed which provides for unobstructed viewing within a body space of a patient. The endoscopic device includes a tube carrying a light transmitting system with a balloon extending over the system. The balloon can be expanded and the interior of the body space inspected or irradicated with a laser beam through the balloon.

24 Claims, 9 Drawing Figures

U.S. Patent   Sep. 11, 1984   Sheet 1 of 3   4,470,407
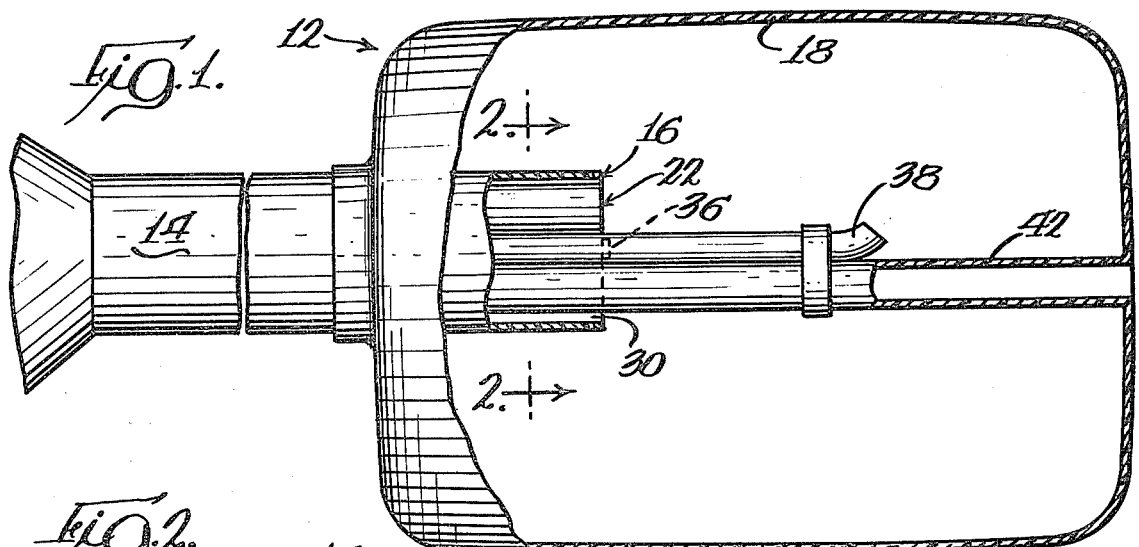
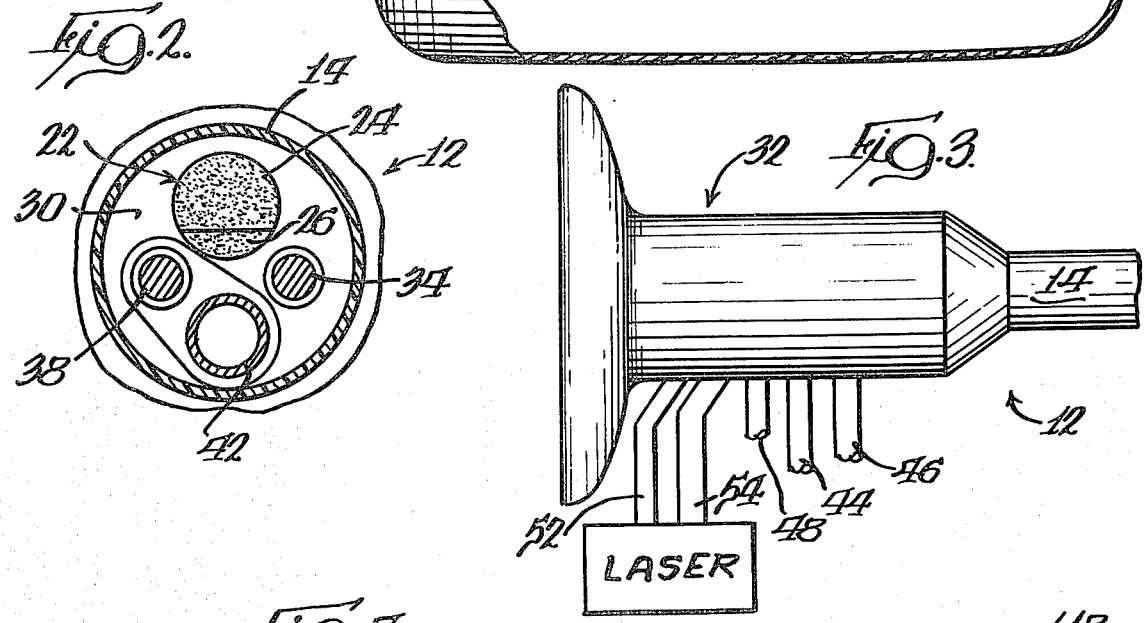
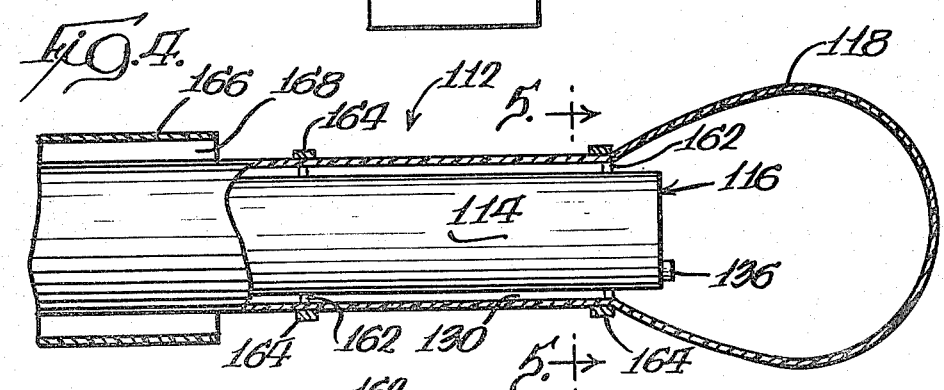
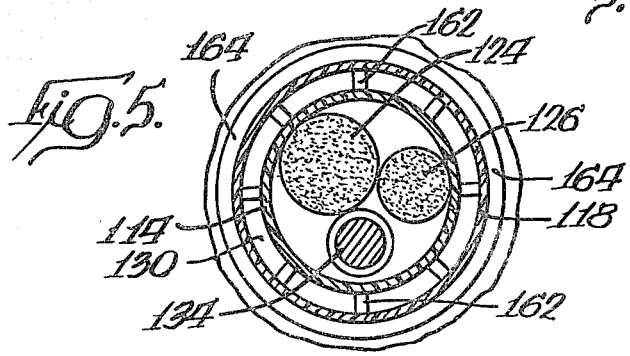

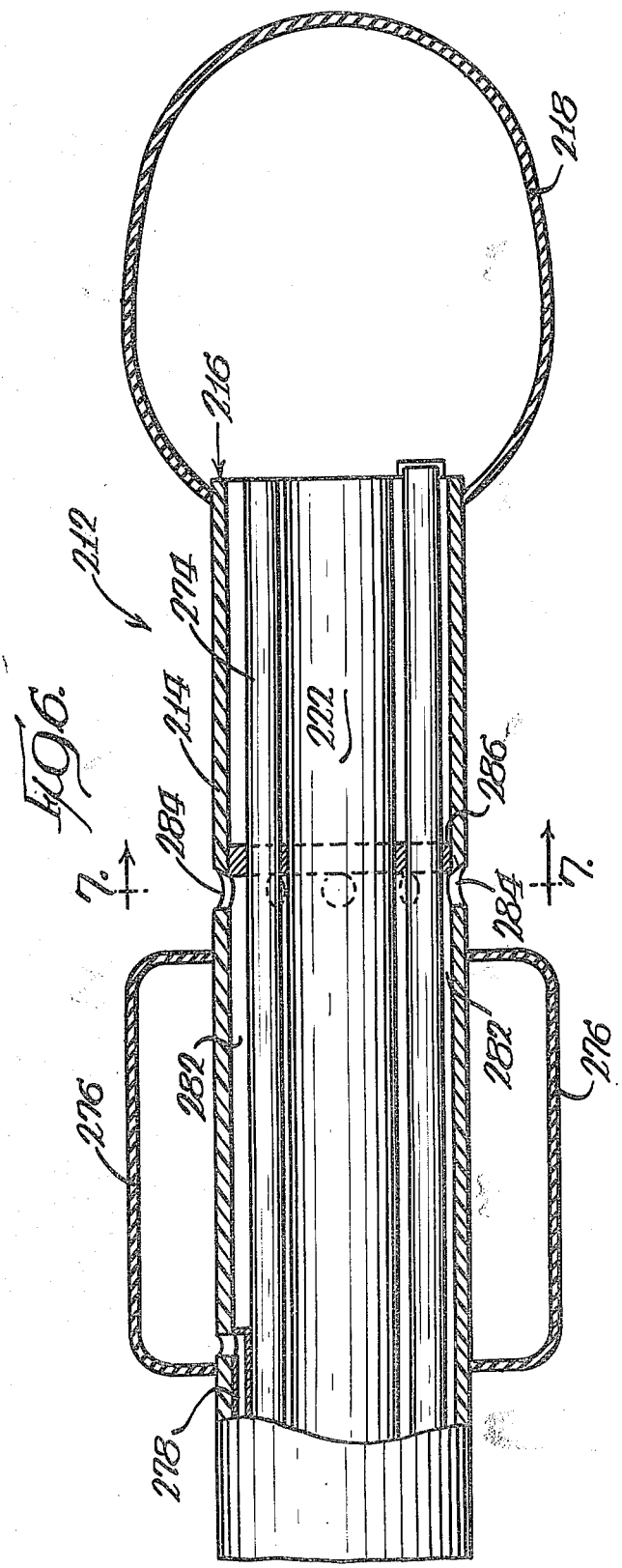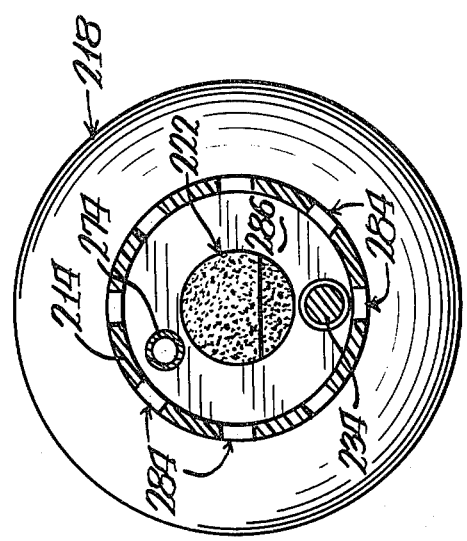

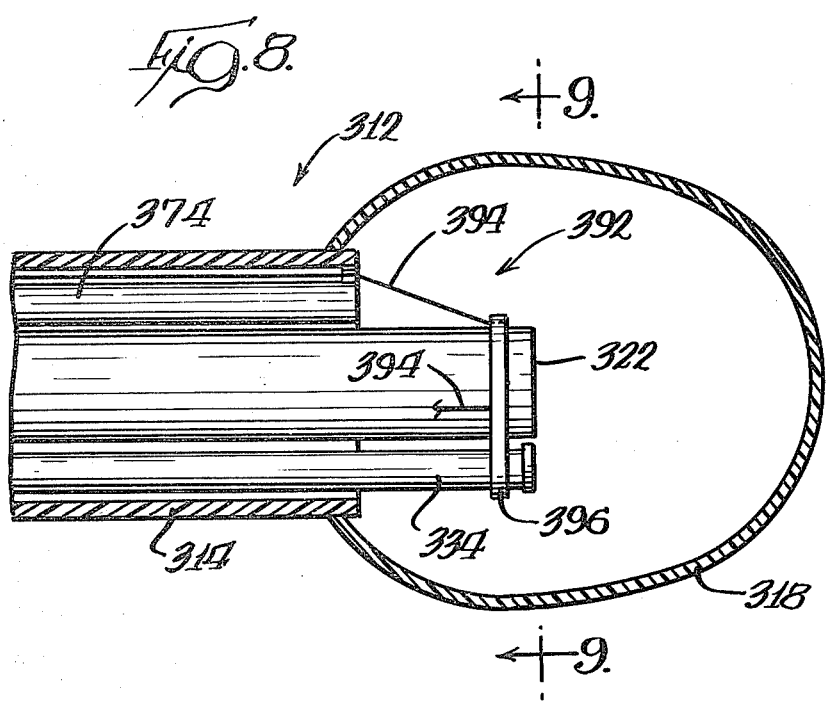
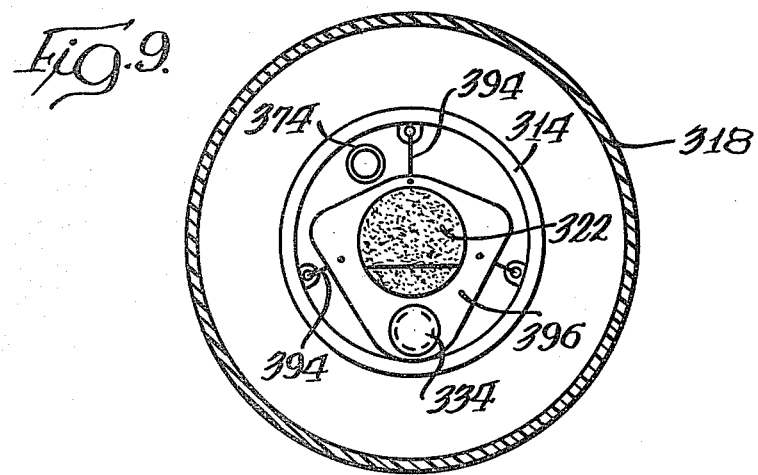

ENDOSCOPIC DEVICE

TECHNICAL FIELD

This invention relates to medical devices for use in a body space within a patient and in particular endoscopic devices which permit viewing within the body space.

BACKGROUND OF THE INVENTION

Endoscopes are used by physicians to inspect and occasionally perform medical procedures within a body space in a patient such as a lumen or cavity. Generally, an endoscope has an elongated tube which carries a viewing system, such as a fiberoptic system, for viewing through the length of the endoscope. The distal end of the endoscope is first inserted into the patient's body space through a natural or surgical opening. The physician can then inspect that portion of the body space beyond the distal end by looking through coupling optics mounted on the proximal end of the endoscope.

Unfortunately, early endoscopes could not operate in opaque lumen fluids, such as blood in the blood vessels. To obviate this problem, inflatable balloons were placed circumferentially about the endoscope tube and inflated to seal the blood vessel. A clear flushing fluid such as saline is then introduced into the blood vessel to displace the blood and provide a clear view. However, even this approach has its shortcomings.

The viewing systems often fail because debris collects on the distal end of the system, obstructing the view. In addition, where the endoscope includes a laser light transmitting fiber, debris often becomes charred and bonded to the end of the fiber during use. Attempts to alleviate these problems by directing a flow of flushing fluid over the ends of the fiberoptic bundle and laser fiber have met with only limited success. As long as lumen fluid can come in contact with the ends of the viewing system or laser fiber, they can quickly be rendered inoperative.

Accordingly, it is desirable to provide an endoscopic device which avoids the difficulties of the prior art and provides unobstructed and continuous viewing within a patient's body space. It would also be desirable if such a device prevented debris collection on the end of the viewing system or laser light transmitting fiber. The present invention satisfies these desires.

SUMMARY OF THE INVENTION

The present invention is an endoscopic device which provides for unobstructed use of an optic system within a body space such as a lumen or cavity of a patient. The endoscopic device includes an elongated tube carrying an expandable balloon on the exterior of the distal portion of the tube. The tube also carries an optic system which terminates within the balloon. The optic system can be a viewing system, means for emitting laser irradiation such as a laser light transmitting fiber, or a combination of both. The balloon is substantially transparent when expanded so that a beam of light can pass through.

The distal portion of the endoscopic device can be located within a lumen or cavity and the balloon expanded until it contacts the walls of the lumen or cavity. Any opaque fluid such as blood is displaced by the balloon to provide a clear view from the viewing system through the balloon to the walls. The site on the wall to be viewed can be contacted by the balloon and viewed through the balloon. Flushing of the lumen is not necessary. Thus, a flushing fluid channel is unnecessary and the outside diameter of the endoscopic device can be kept relatively small.

The present invention has other advantages useful in lumens having either clear or opaque fluids. As an example, for a site within a lumen to be in focus through a viewing system there must be at least a specific distance between the terminal end of the system and the site. This distance is chosen by the focusing lens on the terminal end of the system. The size of the balloon can provide the proper spacing between the terminal end of the viewing system and the lumen site being inspected to insure proper focus.

The present invention also provides a clearer view because the light passes through less body fluid. The interior of the balloon contains a clear fluid such as carbon dioxide or saline which do not distort viewing as much as the same thickness or depth of body fluid. In addition, by altering the index of refraction of the fluid placed within the balloon, it is also possible to create a lens effect with the curved surface of the balloon.

The present invention also has particular advantages over the prior art where the endoscopic device includes means for emitting laser irradiation through the balloon such as a laser light transmitting fiber. The balloon, because it is spaced from the end of the laser light transmitting fiber, protects that end from the collection of debris. The viewing system is similarly protected. The balloon also displaces lumen fluid to provide the desired proper spacing and a less distorting beam path as was described above for the viewing system. Thus, it is possible to both inspect the interior of the lumen and treat it with laser irradiation while avoiding the problems inherent with prior devices.

The laser light transmitting fiber can direct laser irradiation at an angle with respect to the axis of the device to remove plaque from the walls of a blood vessel. The end of the laser fiber can be preset at an angle and directed by rotating the device within the lumen or by being bendable as by wires as is known in the art. The viewing system can be similarly directable.

Dr. Andreas Gruntzig of Switzerland has developed a method of dilating constricted blood vessels as described in U.S. Pat. No. 4,195,637 to Gruntzig et al. A balloon is passed through a blood vessel, located within the constricted portion, and inflated to compress plaque and open the vessel. Unfortunately, the Gruntzig process does not allow for viewing immediately before, during or after this procedure. The physician is unable to tell immediately whether the process was a success or whether some possibly undesirable or even dangerous condition has developed.

The present invention allows such viewing. The balloon can be placed in a constricted portion of the lumen and expanded forcing the constriction into the walls. The physician can observe through the balloon the effect the expanding balloon has on the constriction and walls of the lumen. Should it appear that any detrimental damage is being done, the physician can immediately stop the process before any further damage takes place. This was not possible with the prior devices.

Numerous other advantages and features of the present invention will become readily apparent from the following detailed description of the invention, the accompanying examples, the drawings, and the appended claims.

BRIEF DESCRIPTION OF THE DRAWINGS

FIG. 1 is a fragmentary view, partly broken away to show interior detail and partly in section, of the distal portion of an endoscopic device embodying the present invention;

FIG. 2 is a cross-sectional view taken along plane 2—2 of FIG. 1 showing the internal structure of the endoscopic device;

FIG. 3 shows the proximal portion of the endoscopic device of FIG. 1;

FIG. 4 is a fragmentary view, partly in section, showing the distal portion of an alternative endoscopic device embodying of the present invention;

FIG. 5 is a cross-sectional view taken along plane 5—5 of FIG. 4 showing the internal structure of the alternative embodiment;

FIG. 6 is a fragmentary view, partly in section, showing the distal portion of a further alternative endoscopic device embodying the present invention;

FIG. 7 is a cross-sectional view taken along plane 7—7 of FIG. 6 showing the internal structure of the alternative embodiment;

FIG. 8 is a fragmentary view, partly in section, showing the distal portion of a still further alternative endoscopic device embodying the present invention; and FIG. 9 is a cross-sectional view taken along plane 9—9 of FIG. 8.

DETAILED DESCRIPTION OF THE PREFERRED EMBODIMENTS

While this invention is susceptible to embodiment in many different forms, there are shown in the drawings and will be described in detail, preferred embodiments of the invention. It should be understood, however, that the present disclosure is to be considered as an exemplification of the principles of this invention and is not intended to limit the invention to the embodiments illustrated.

For ease of description the endoscopic device of this invention will be described with the term "distal" as referring toward the end which is inserted in the patient and the term "proximal" as referring toward the end which remains outside the patient.

One embodiment of the present invention, an endoscopic device 12 is shown in FIGS. 1-3. The endoscopic device 12 includes an elongated tube 14 carrying an expandable balloon 18 on the exterior of the distal portion of the tube. The elongated tube 14 is preferably flexible to allow it to be manipulated through various body spaces such as lumens and cavities. In this embodiment, the balloon is preferably sealingly mounted about the periphery of the tube 14 adjacent the distal end 16 with the balloon extending over the distal end.

The endoscopic device 12 also includes an optic system carrier by the tube 14 and terminating within the balloon 18. The optic system can be means for emitting laser irradiation (discussed below), a viewing system, or a combination of both. A portion of the tube 14 can also extend distally of the balloon provided the optic system nevertheless terminates within the balloon.

The viewing system 22 has an optical viewing conduit 24, coupling optics, most of which are carried by a handle 32 on the proximal end of the tube, and means for emitting light within the expandable balloon such as a light transmitting bundle 26. Where a laser light transmitting fiber is provided, it can serve as the light transmitting bundle. The viewing conduit 24 can be a flexible fiberoptic viewing bundle, a thin lens system, a rod lens system, or a graded index (GRIN) system. The operation of viewing conduits and coupling optics is well-known in the art and need not be described in further detail.

The endoscopic device 12 also includes a fluid passageway 30 in fluid communication with the balloon for expanding the balloon. The fluid passageway can be defined by a separate tubule carried by the elongated tube 14 or it can be defined by the interstitial space around the viewing system 22 and any other structures carried within the tube. The latter approach is preferred because it minimizes the space needed within the tube 14 to provide for expansion of the balloon. The expandable balloon 18 is substantially transparent when expanded. The term "substantially transparent" as used herein means that a discernable image can be seen through the balloon using the viewing system.

Preferably, the endoscopic device also includes, in lieu of or together with the viewing system, means for emitting laser irradiation through the balloon. This can be any suitable means such as a laser light transmitting fiber 34 which is carried by the tube 14 and terminates within the balloon 18. The laser light transmitting fiber 34 can be aimed along the axis of the tube and focused by a focusing lens 36. The laser light transmitting fiber can instead be positioned such that it emits laser irradiation at an acute angle with respect to the axis of the tube. Alternatively the fiber can be provided with means for directing the end to aim the emitted irradiation, e.g. wires, discussed below.

A second laser light transmitting fiber 38 as shown in FIG. 1 performs such a function. Either laser light transmitting fiber can be provided alone, or both can be provided. Thus, it is possible to direct laser irradiation toward the front of the device to remove obstructions within the lumen or cavity or to direct laser irradiation at the walls of the lumen or cavity, for example, as is useful in removing plaque in a blood vessel. The laser light transmitting fibers are operably associated with a laser source which is connected to the endoscopic device through the handle 32.

The handle 32 is provided with a pair of fluid connectors 44, 46 to place the fluid passageway 30 and hose 42 respectively in fluid communication with a vacuum or pressure source (not shown). A light source connector 48 is provided for operably associating the light transmitting bundle 26 with a light source (not shown). The handle also includes a pair of laser light connectors 52, 54 for placing the laser light transmitting fibers in communication with the laser.

Both laser light transmitting fibers can be aimed by rotating the tube 14. The "straight" fiber 34 because it is offset with respect to the axis of the tube 14 and balloon 18 emits its beam along differing paths as the tube is rotated. The "curved" fiber 38 also emits its beam at differing sites depending on the position of the tube. The viewing system can also be "curved" similar to fiber 38 to facilitate inspection of the lumen walls.

The laser light transmitting fibers can be used to cauterize bleeding tissue, or to remove tissue, blockage or deposits from within a lumen. The laser fibers can also be used to direct laser irradiation at the walls of a lumen or body cavity to create a new channel within the patient's tissue.

The endoscopic device 12 can also include hose 42 which is carried by the elongated tube 14 and extends beyond the distal end 16 of the tube and through the balloon 18 to place the hose in fluid communication with the lumen distally of the balloon. This permits the introduction of a clear flushing fluid such as carbon dioxide or saline into the lumen to enable viewing and laser use beyond the distal end of the balloon. A physiologically compatable, oxygen bearing fluid can also be introduced through the hose 42 to provide oxygen to tissues downstream of the device. The hose 42 can also extend distally of the balloon.

Where the site to be treated is on the wall of the lumen or cavity, the balloon can be expanded to contact the wall or forced into contact with the wall, thus displacing any fluid from between the balloon and wall. This provides a clear viewing and irradiation pathway between the distal end of the tube and the site to be treated. It is not necessary to displace an opaque fluid with a clear flushing fluid. For such applications, the tube 14 need not be large enough to include a flushing fluid hose and thus can fit into smaller lumens.

Where it is desirable to view and treat tissue beyond the distal end of the tube, the present invention has particular advantages over the prior art. To be able to view and use a laser on a site within a lumen, it is desirable that the distal end of the tube be spaced from the site. With the present invention, much of the distance between the distal end 16 and the site is within the expandable balloon 18. Because the fluid placed in the expandable balloon, such as carbon dioxide or saline is clear, there is little optical distortion and irradiation attenuation. With the hose 42, it is possible to view through the distal end of the balloon in a blood vessel by displacing the blood with a clear fluid.

The balloon 18 is made of a flexible material which is preferably elastomeric. When used with a laser, the balloon should be contructed of a material which can transmit laser irradiation without being substantially damaged. That is, there can be some slight damage to the balloon by the laser irradiation, but the integrity of the overall structure of the balloon remains unchanged. The type of material used to construct the balloon can vary depending on the type of laser to be used. The balloon material should preferably have a relatively high melting temperature. The heat generated in body tissue during laser irradiation can be conducted to the balloon where it contacts the tissue. One such flexible material is a copolymer of vinyl chloride and vinylidene chloride commercially available under the trademark SARAN from Dow Chemical Company. A SARAN balloon can be manufactured in a sack-like configuration with any seams located toward the inside of the balloon to prevent damage to the lumen walls.

A SARAN balloon can be used with an Argon and YAG laser. Another material suitable for the balloon is a substantially clear natural rubber. A natural rubber balloon can also be used with a YAG laser. A substantially transparent, natural rubber balloon material is prepared by curing latex on form in the desired shape of the balloon. The balloon can then be sealingly mounted on the distal portion of the tube.

As an example, a polished aluminum mandrel of about 3 millimeters in diameter is dipped into a latex formulation at the rate of about 0.5 centimeters per second. The latex formulation is one which when cured becomes substantially clear such as a natural rubber having a low content of dissolved solids available from Edmont-Wilson, a division of Becton-Dickinson and Company. The mandrel is removed from the rubber and any excess latex is removed.

The mandrel is then rotated about its axis at about 50 rpm to provide a uniform thickness to the latex adhering to the mandrel. The adhering latex and mandrel are placed in a 75 degree C. oven for about 5 minutes. The mandrel is then cooled to room temperature and redipped into the latex and rotated as described above. This increases the thickness of the balloon.

The adhering latex and mandrel are then placed in a 75 degree C. oven for about 10 minutes, After cooling, the mandrel and adhering latex are placed in a 36 degree C. water bath for about 30 minutes to leach the balloon. The mandrel is then placed in a 100 degree C. oven for about 10 minutes. The adhering latex and mandrel are then allowed to cool to room temperature and rest for 24 hours. The mandrel is then cooled as being submerged in liquid coolant, e.g., Freon, for about two minutes so the balloon can be removed. The balloon, when expanded, preferably has a thickness of about 0.001 in. to about 0.003 inches. Other materials for the balloon include polyethylene terephthalate commercially available under the trademark MYLAR, polyurethane elastomers, polyethylene, and the like.

An alternative embodiment for the endoscopic device is shown in FIGS. 4 and 5. In this embodiment the endoscopic device 112 includes a balloon 118 which extends substantially along the length of the tube 114. The fluid passageway 130 is defined by the space between the balloon and the tube. With this embodiment it is unnecessary that the fluid passageway be located within the tube, but it can be carried along the outer surface of the tube. The balloon can be heat shrunk on the tube 114 so that the fluid passage 130 requires relatively little space.

As before, the elongated tube 114 carries the viewing system which includes a viewing conduit 124 and a light transmitting bundle 126. The tube also carries a laser light transmitting fiber 134 which is provided with a focusing lens 136.

While the expandable balloon can take any configuration, the balloon 118 shown in FIG. 4 has some particular advantages. The distal portion of the balloon is nearly spherical and the interface between fluid in the balloon and lumen fluid can serve as a lens. The liquid in the lumen outside the balloon, either clear saline or natural lumen liquid usually has an index of refraction of approximately 1.35. By placing a low index of refraction fluid, such as carbon dioxide within the balloon, the balloon interface along the distal portion serves as a plano-convex lens. This, in conjunction with the focusing lens 136, can provide a wide angle lens effect when viewing material distally of the device.

The focusing of the viewing system can thus be altered by changing the index or refraction of the fluid within the balloon 118. A low index of refraction fluid in the balloon such as a carbon dioxide (index of refraction about 1.0) provides a divergent lens and a wide angle view. A higher index of refraction fluid such as an 85 percent sucrose solution (index of refraction about 1.5) provides a convergent lens and magnification. A saline solution in the balloon will provide no lens effect when the lumen liquid has a similar index of refraction.

The balloon 118 is maintained in spaced relationship with respect to the tube 114 by spacers 162 along its length. Collars 164 can also be located around the periphery of the balloon to maintain it close to the tube. A collar is particularly useful when located adjacent the distal end 116 of the tube as shown in the drawing. The endoscopic device can also be provided with an external catheter 166 which surrounds the tube 114 and terminates proximally at the distal end 116 of the balloon. The external catheter 166 and tube together with the surface of the balloon 118 define a duct 168 through which flushing fluid can be introduced. The external catheter 166 can also be used to position the distal end of the endoscopic device within the lumen.

A still further embodiment of the present invention can be seen in FIGS. 6 and 7. As before, the endoscopic device 212 has an elongated tube 214 having distal end 216 and carrying a viewing system 222. The elongated tube 214 also carries a laser light transmitting fiber 234 and an expandable balloon 218 which preferably extends over the distal end 216 of the tube. A tubelet 274 is also carried by the tube 214 in fluid communication with the balloon for introducing fluid to expand the balloon.

In this embodiment, the tube 214 also carries a second balloon 276 spaced proximally of the expandable balloon 218. The second balloon 276 is adapted to be expanded to seal with the inside of a lumen to occlude the flow of blood within a blood vessel. The second balloon need not be transparent. A second tubelet 278 is carried by the tube 214 in fluid communication with the second balloon 276 for expanding the second balloon.

The interstitial space between the viewing system 222, the laser light transmitting fiber 234, and the tubelets 274, 278 within the elongated tube 214 defines a fluid duct 282 in communication with one or more ports 284 in the sides of the tube 214. A bulkhead 286 seals about the structures within the tube to prevent the flow of flushing fluid to the distal end 216 of the tube.

In operation, the distal portion of the medical device as shown in FIGS. 6 and 7 can be located within a lumen such as a blood vessel. The second balloon 276 then is expanded to contact the walls of the blood vessel and occlude the flow of blood. A clear flushing fluid such as saline or carbon dioxide can then be introduced into the fluid duct 282. The flushing fluid then passes down the duct, to the bulkhead 282 where it exits the tube ports 284. The flushing fluid then passes over the distal end of the tube and balloon displacing any opaque fluid such as blood. The expandable balloon 218 is then expanded and used for viewing laser use as described above.

This design has the particular advantage of providing a second balloon 276 which occludes the flow of blood as well as maintaining the position of the tube 214 within a blood vessel. A clear view is then provided not only within the expandable balloon 218, but also outside that balloon in the surrounding lumen area. Thus, the benefits of having the viewing system and laser light transmitting fiber terminating within the expandable balloon 218 are increased by having a substantially clear flushing fluid outside the balloon.

A still further embodiment of the present invention can be seen in FIGS. 8 and 9. As before, the endoscopic device 312 has the optic system carried by the tube 314 and terminating within the expandable balloon 318. The balloon is expanded by fluid entering through the tubelet 374. In this embodiment the optic system which includes a viewing system 322 and laser light transmitting fiber 334, extends a distance into the balloon 318 from the tube 314. Also included are control means 392 for tilting the terminal end of the optic system with respect to the axis of the tube 314.

The control means can be any suitable means for tilting the optic system such as one or more wires 394 operably associated with the terminal end of the optic system as by being connected to a plate 396 attached to the terminal end. As tension is placed on one of the wires 394, the viewing system 322 and the laser light transmitting fiber 334 are tilted and aimed at a desired location on the lumen wall.

The foregoing specification is intended as illustrative and is not to be taken as limiting. Still other variations within the spirit and scope of this invention are possible and will readily present themselves to those skilled in the art.

What is claimed is:

1. An endoscopic device for use in a body space comprising:
   (a) an elongated tube having a distal portion;
   (b) an expandable balloon carried on exterior of the distal portion of the tube, the balloon being substantially transparent when expanded;
   (c) a fluid passageway in fluid communication with the expandable balloon;
   (d) an optic system carried by the tube and terminating within the expandable balloon; and
   (e) a hose carried by the tube and extending beyond the distal portion of the tube and through the expandable balloon to be in fluid communication with the body space distally of the balloon;
   whereby the distal portion of the endoscopic device can be inserted into the body space and fluid introduced through the fluid passageway to expand the expandable balloon.

2. The endoscopic device of claim 1 wherein the expandable balloon extends over the distal portion of the tube.

3. The endoscopic device of claim 1 wherein the optic system includes a viewing system.

4. The endoscopic device of claim 3 further including means for emitting laser irradiation through the balloon and wherein the expandable balloon is constructed of a material which can transmit laser irradiation without being substantially damaged.

5. The endoscopic device of claim 1 wherein the optic system includes means for emitting laser irradiation through the expandable balloon.

6. The endoscopic device of claim 1 wherein the balloon extends substantially along the length of the tube and the fluid passageway is defined by the space between the balloon and the tube.

7. The endoscopic device of claim 1 wherein the fluid passageway is carried within the tube.

8. The endoscopic device of claim 1 wherein the expandable balloon is sealingly mounted about the periphery of the tube adjacent the distal portion.

9. The endoscopic device of claim 1 wherein the expandable balloon is constructed of an elastomeric material.

10. The endoscopic device of claim 1 wherein the expandable balloon has a thickness of about 0.001 inches to about 0.003 inches when expanded.

11. The endoscopic device of claim 1 wherein the expandable balloon is constructed of a material selected from the group consisting of natural rubber, a copolymer of vinyl chloride and vinylidene chloride, polyurethane, polyethylene, polyethylene terephthalate, and composites thereof.

12. The endoscopic device of claim 1 including an external catheter received about the tube and terminating proximally of the distal portion of the tube, the catheter and balloon together defining a duct therebetween.

13. The endoscopic device of claim 1 further including control means for tilting the terminal end of the optic system with respect to the axis of the tube.

14. The endoscopic device of claim 13 wherein the control means includes at least one wire operably associated with the terminal end of the optic system.

15. An endoscopic device for use within a body space of a patient, the device comprising:
 (a) an elongated tube having a distal end;
 (b) an expandable balloon sealingly mounted about the periphery of the tube adjacent the distal end and extending over the distal end, the expandable balloon being substantially transparent when expanded and constructed of a material which can transmit laser irradiation without being substantially damaged;
 (c) a fluid passageway carried by the tube in fluid communication with the expandable balloon;
 (d) a viewing system carried by the tube and terminating within the expandable balloon; and
 (e) a laser light transmitting fiber carried by the tube and terminating within the expandable balloon;
 whereby the distal end of the device can be received within the body space and the expandable balloon expanded to contact the body space walls such that the inside of the space can be inspected and subjected to laser irradiation.

16. The endoscopic device of claim 15 wherein the expandable balloon is constructed of an elastomeric material.

17. The endoscopic device of claim 15 wherein the expandable balloon has a thickness of about 0.001 inches to about 0.003 inches when expanded.

18. The endoscopic device of claim 15 wherein the expandable balloon is constructed of a material selected from the group consisting of natural rubber, a copolymer of vinyl chloride and vinylidene chloride, polyurethane, polyethylene, polyethylene terephthalate, and composites thereof.

19. The endoscopic device of claim 15 wherein the laser light transmitting fiber is curved to emit laser radiation at a non-parallel angle with respect to the axis of the tube.

20. The endoscopic device of claim 15 further including a second balloon carried by the tube spaced proximally of the expandable balloon, the second balloon being adapted to be expanded to seal with the inside of a lumen.

21. The endoscopic device of claim 20 further including a fluid duct defined by the tube and opening through at least one port in the side of tube between the expandable balloon and the second balloon.

22. The endoscopic device of claim 15 further including control means for tilting the terminal end of the viewing system with respect to the axis of the tube.

23. The endoscopic device of claim 15 further including control means for tilting the terminal end of the laser light transmitting fiber with respect to the axis of the tube.

24. The endoscopic device of claim 15 including a hose carried by the tube and extending beyond the distal end of the tube and through the expandable balloon to be in fluid communication with the body space distally of the balloon.

* * * * *